US010828063B2

(12) United States Patent
Amann et al.

(10) Patent No.: US 10,828,063 B2
(45) Date of Patent: Nov. 10, 2020

(54) MEDICAL INSTRUMENT

(71) Applicant: RICHARD WOLF GMBH, Knittlingen (DE)

(72) Inventors: Carina Amann, Wurmberg (DE); Friedrich Hähnle, Bretten (DE); Eberhard Körner, Knittlingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 113 days.

(21) Appl. No.: 15/917,283

(22) Filed: Mar. 9, 2018

(65) Prior Publication Data

US 2018/0263656 A1 Sep. 20, 2018

(30) Foreign Application Priority Data

Mar. 10, 2017 (DE) .................. 10 2017 204 010

(51) Int. Cl.
*A61B 17/34* (2006.01)
*A61B 17/04* (2006.01)
*A61B 17/062* (2006.01)
*A61B 17/28* (2006.01)
*A61B 90/00* (2016.01)
(Continued)

(52) U.S. Cl.
CPC ...... *A61B 17/3403* (2013.01); *A61B 17/0483* (2013.01); *A61B 17/062* (2013.01); *A61B 17/2833* (2013.01); *A61B 17/3478* (2013.01); *A61B 90/03* (2016.02); *A61B 2017/00367* (2013.01); *A61B 2017/00477* (2013.01); *A61B 2017/2946* (2013.01); *A61B 2017/3409* (2013.01)

(58) Field of Classification Search
CPC ............ A61B 17/3403; A61B 17/0483; A61B 17/062; A61B 17/2833; A61B 17/3478; A61B 17/2909; A61B 17/0487; A61B 17/2841; A61B 90/03; A61B 2017/00367; A61B 2017/00477; A61B 2017/2946; A61B 2017/3409; A61B 2017/292; A61B 2017/2919; A61B 1/0052; A61B 1/00066; A63F 2011/0044; A47J 43/26; B26F 2001/365; B21F 1/002
See application file for complete search history.

(56) References Cited

FOREIGN PATENT DOCUMENTS

DE      42 07 124 C1    6/1993
DE      600 04 125 T2    4/2004
(Continued)

*Primary Examiner* — Erich G Herbermann
(74) *Attorney, Agent, or Firm* — McGlew and Tuttle, P.C.

(57) ABSTRACT

A medical instrument includes a proximal handle (3), for controlling a distal tool, including two grip pieces (4, 5) pivotable relative to one another, subjected to spring force and coupled in movement via a path guide with a path component (7). The path component includes a guide path (11), and a guide body (14) on a guide component (8). The guide body engages into the guide path. The components (7, 8) are arranged on one of the grip pieces and are subjected to a spring force, transversely to a pivoting plane of the grip pieces. One of the components (8) is pivotably arranged on a grip piece. Functionally independent of the guide body (14) and guide path (11), a latching body (12) is received by a latching receiver (16) on the components (7, 8) for a latching function, blocking pivoting movement of the grip pieces.

13 Claims, 6 Drawing Sheets

(51) Int. Cl.
*A61B 17/29* (2006.01)
*A61B 17/00* (2006.01)

(56) References Cited

FOREIGN PATENT DOCUMENTS

DE  10 2014 110 881 A1   2/2016
WO  WO-2015168441 A1 * 11/2015  ............. A61B 34/71

* cited by examiner

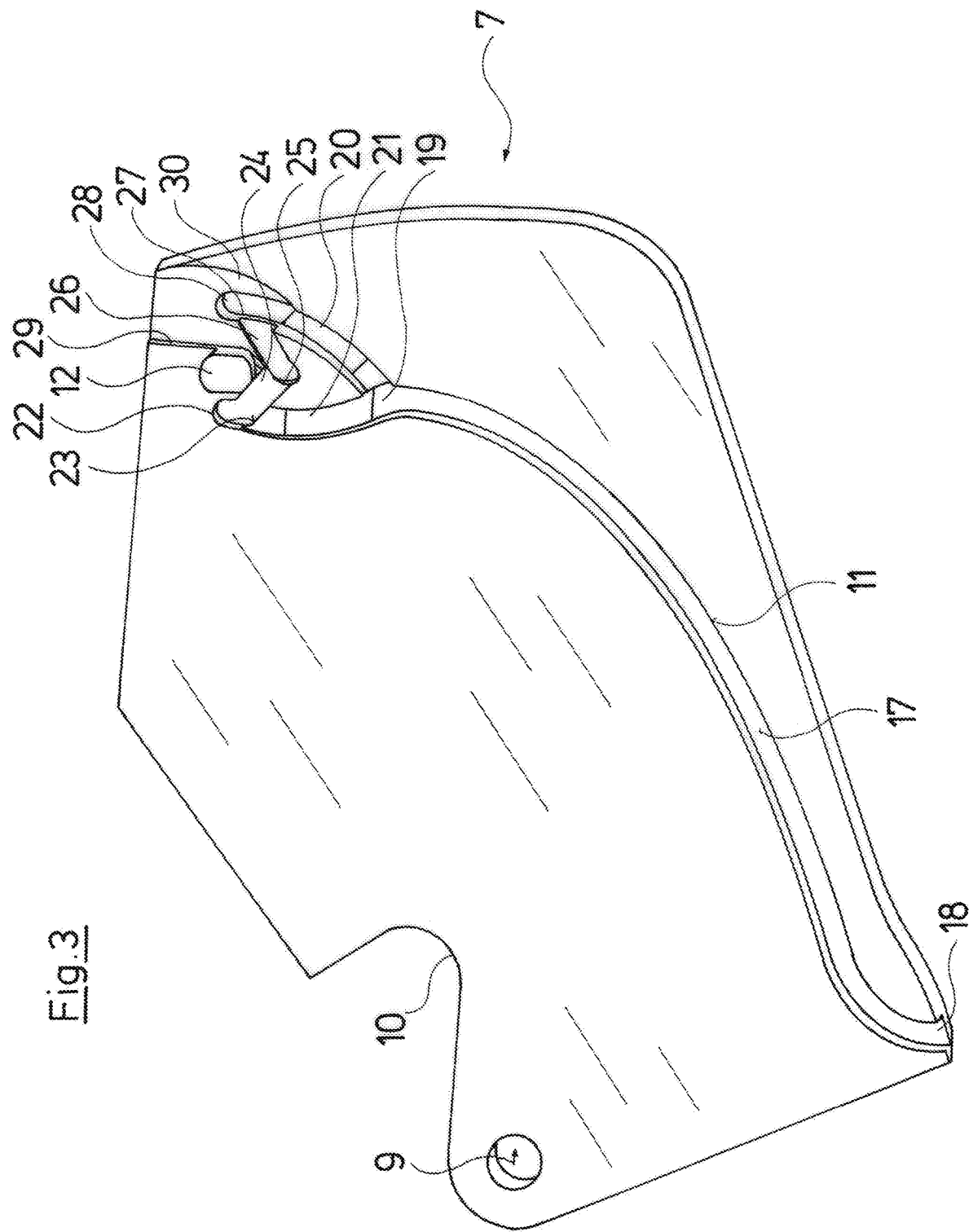

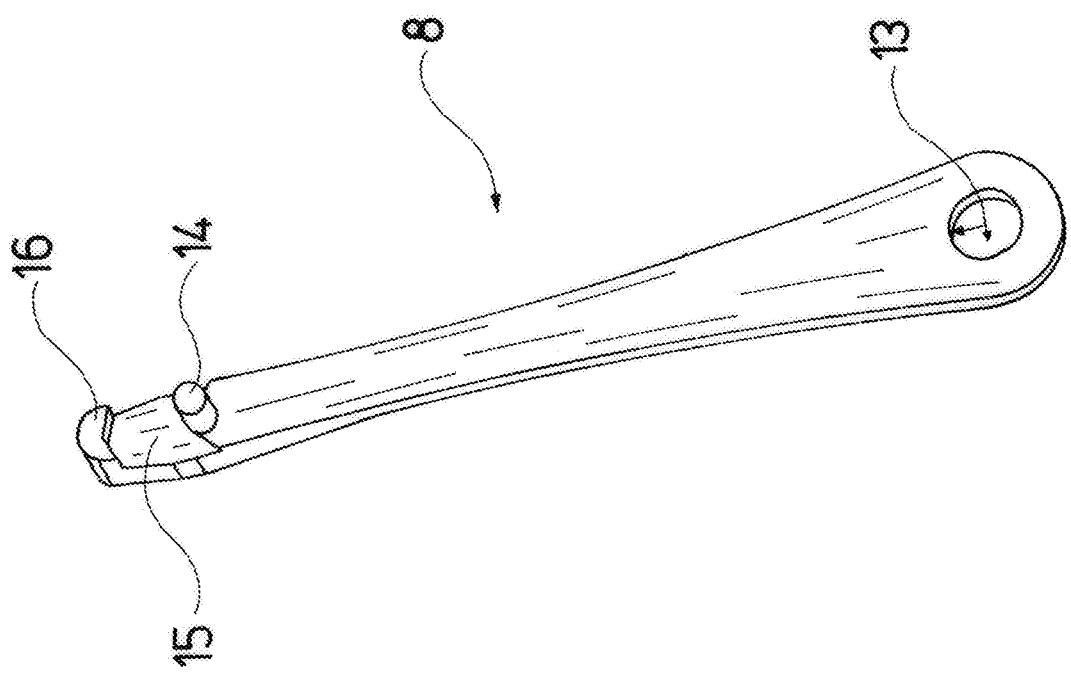

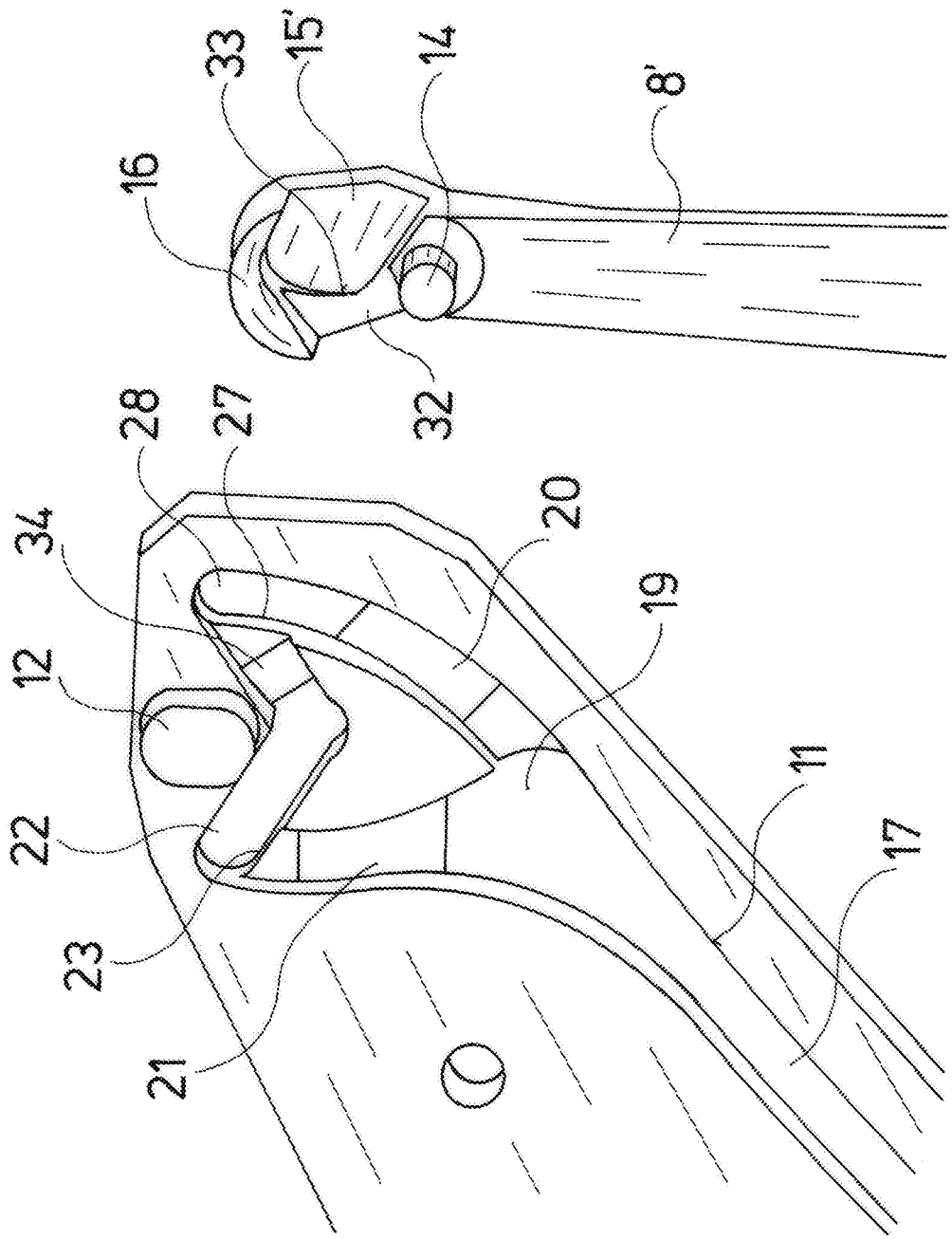

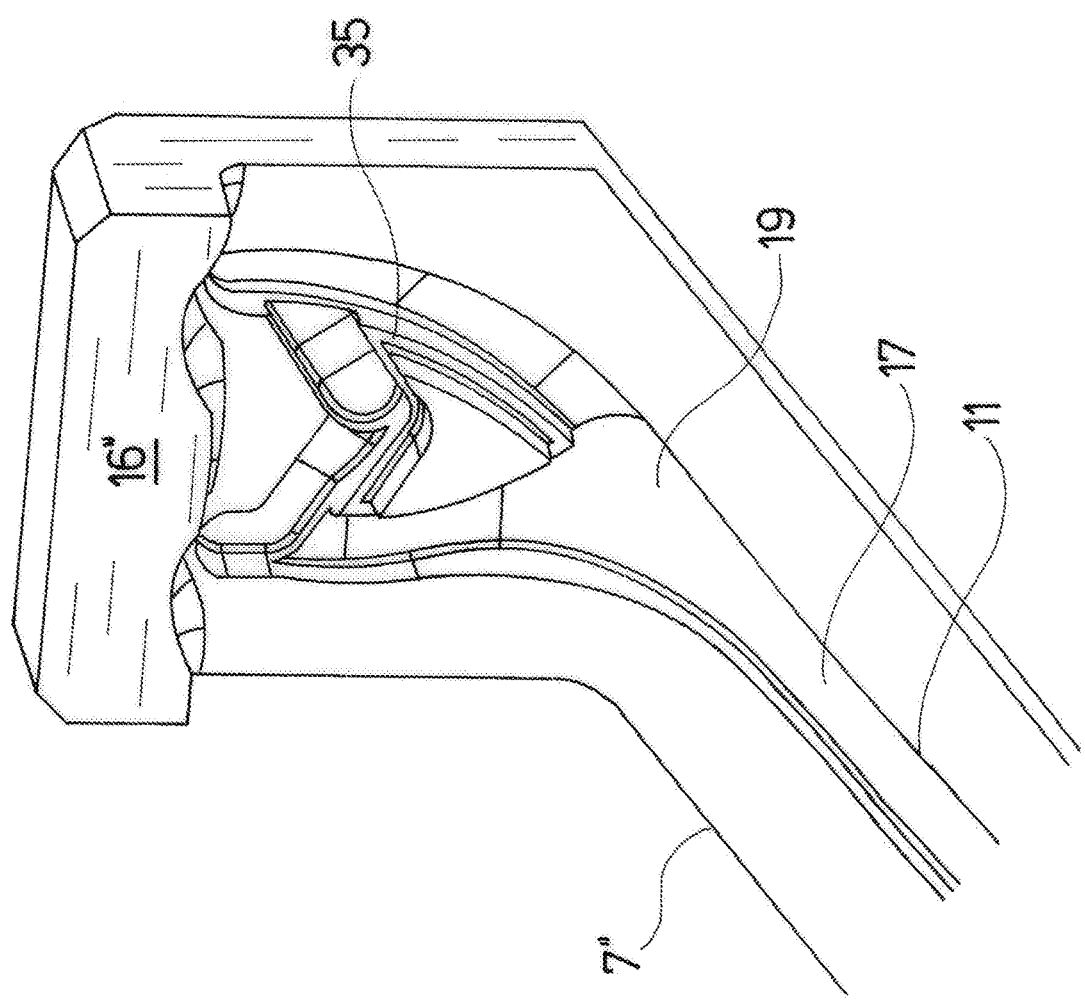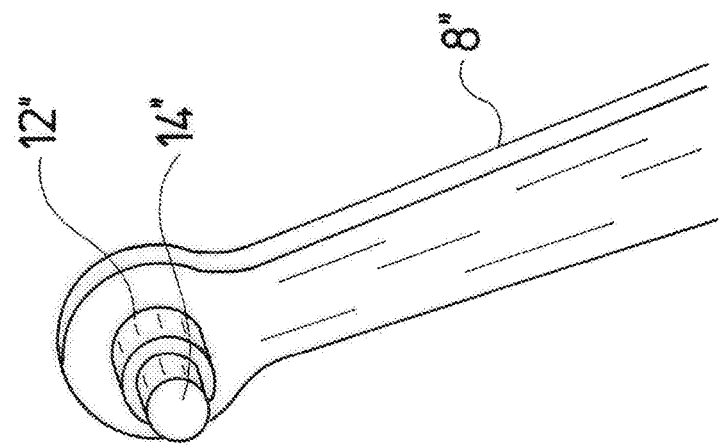

MEDICAL INSTRUMENT

CROSS REFERENCE TO RELATED APPLICATIONS

This application claims the benefit of priority under 35 U.S.C. § 119 of German Application 10 2017 204 010.6, filed Mar. 10, 2017, the entire contents of which are incorporated herein by reference.

FIELD OF THE INVENTION

The invention relates to a medical instrument, in particular to an endoscopic instrument with a proximal handle, for controlling a distal tool, comprising two grip pieces which are arranged in a pivotably movable manner relative to one another, are subjected to spring force and are coupled in movement to one another via a path guide.

BACKGROUND OF THE INVENTION

A medical instrument of this type is known from DE 42 07 124 C1. Here, it is a medical instrument such as for example a clamp, a forceps, a needle holder or the like, which at the proximal side comprises a handle for controlling a distally arranged tool, wherein the handle comprises two grip pieces which are arranged in a pivotably movable manner relative to one another and are impinged by spring force. These grip pieces are coupled in movement to one another via a path guide which is arranged between the grip pieces, wherein the path guide consists of a path component which comprises the guide path and is articulated on a grip piece, and of a guide component which is arranged on the other grip piece and comprises a guide body, wherein the guide body is engaged with the guide part. Herein, the grip pieces are subjected to a spring force to one another and the guide body is moreover subjected to spring force in the direction of the base of the guide path, by which means the peripheral direction of the guide body in the guide path is defined at least in sections. Several latching positions are provided within the guide path, into which positions the guide body can engage, so that on pressing together the grip pieces, these can latch into one of the latching positions, wherein on further pressing together the grip pieces, the respective latching position releases and the grip pieces can be moved into the next latching position or moved apart again due to spring force. These latching positions are provided, in order to fix the distal tool, for example a needle holder in the holding function and to subsequently release it again.

The disadvantage with this known design is the fact that on account of the open arrangement in the proximity of the proximal ends of the grip pieces, there exists the danger of a foreign body getting into the latching mechanism and inhibiting its reliable functioning. The components between the grip pieces must be designed in an adequately stable manner, in order to apply the necessary spring force as well as to ensure the holding force function, and this renders the instrument heavy and awkward.

A similar latching mechanism is known from DE 10 2014 110 881 A1. Here too, a guide body is engaged with a guide path, wherein the guide body not only assumes the guiding function within the guide path, but also the holding force in the latching position, so that a miniaturization of the components is hardly any longer possible already on account of the forces which are to be transmitted.

SUMMARY OF THE INVENTION

Against this background, it is an object of the invention to improve a medical instrument of the type according to the preamble, in particular to design it such that the latching mechanism can be further miniaturized without compromising its function.

According to the invention, this object is achieved by a medical instrument. In particular, the medical instrument according to the invention is an endoscopic instrument, thus an instrument with a proximal handle for controlling a distal-side tool, said handle and tool being typically connected to one another and coupled in movement to one another via a shank and a mechanism which is guided therein, e.g. a rod. The proximal handle comprises two grip pieces which are arranged pivotably movable relative to one another, are subjected to spring force and are coupled in movement to one another via a path guide. The path guide comprises a path component which comprises a guide path and a guide body on a guide component, said guide body engaging into the guide path. These components are each arranged on one of the grip pieces and are subjected to spring force to one another transversely to a pivoting plane of the grip pieces. One of these components is pivotably arranged on a grip piece, wherein at least one latching position, in which the pivoting movement of the grip pieces is blocked in one direction, is formed between these components.

According to the invention, in a manner which is functionally independent of the guide body and guide path, a latching body for the latching function is provided, as well as at least one latching receiver which receives the latching body in a latching position, and specifically on the components, i.e. on the guide component and on the path component.

The basic concept of the solution according to the invention is therefore the decoupling of the guiding function and latching function. Since a latching body which is functionally independent of the guide body and guide path, as well as a latching receiver which is envisaged for this are provided for the latching function, the components can be adapted in accordance with the respective functions, i.e. only the latching body and the latching receiver are to be dimensioned for accommodating relatively large holding forces which arise when the grip pieces are held in the closed position, i.e. the tool, e.g. the needle holder is held in the closed position. In contrast, the guide body and guide path can be dimensioned with a view solely to guiding function during the movement course, i.e. on pivoting the grip pieces to one another and on pivoting back due to the spring force, by which means this can entail a significant miniaturization which permits these components to be arranged much further distally, thus in the proximity of the joint connection or connections of the grip pieces. The grip pieces are more easily accessible and less prone to a faulty operation or faulty functioning due to the penetration of foreign bodies on account of this.

According to the invention, herein it is basically of no significance as to whether one grip piece is arranged in a fixed manner with regard to the instrument and the other in a pivotable manner or as to whether both grip pieces are pivotably arranged with respect to an instrument body. Moreover, concerning the solution according to the invention, it is of no significance as to whether the subjection of the grip pieces to spring force is envisaged in the opening direction or closing direction. Nevertheless, this is typically effective in the direction of opening, i.e. this spring force must be overcome on pivoting the grip pieces together, which in the opposite direction ensures that the grip pieces including the tool which is connected to these open.

The basic concept of the invention is to therefore decouple the guiding function and the latching function from one another, i.e. to design them functionally independently of one another. It is particularly the guide body and the guide path which can be dimensioned smaller by way of this, which is advantageous. The guide body can typically be conceived as a slim pin, whereas the latching body with the latching receiver can be dimensioned in a larger and more stable manner for accommodating the holding forces of the instrument. Basically, the latching function is designed such that a latching position which holds the grip pieces in their closing position is provided. However, according to the invention, one can also provided several latching positions for intermediate positions and a latching position can also be provided in the opened position of the grip pieces.

Herein, according to the invention, the latching body can be arranged on the path component and the at least one latching receiver on the guide component or also vice versa. The arrangement of the latching body on the path component can be favorable with regard to design if this, in combination with the guide path, already results for reasons of space.

The design of the latching body and the latching receiver can be multifaceted, and in particular can be adapted to the design situations. It is particularly advantageous if, concerning the design with which the latching body is arranged on the path component and the latching receiver on the guide component, the latching body is formed by a stub-like projection whose axis is arranged transversely to a pivoting plane of the grip pieces, wherein the stub is directed in the direction of the guide component and the latching receiver is formed by a projections likewise transversely to a pivoting plane of the grip pieces, but in the direction of the path component. These two parts, specifically the latching body on the one hand and the latching receiver on the other hand are then situated to one another such that in the latching position they engage with their peripheral surfaces. These components with regard to their cross-sectional surfaces are then to be dimensioned in accordance with the forces which are to be accommodated.

Alternatively, according to an advantageous further development of the invention, the latching body is arranged on the guide component and the at least one latching receiver on the path component. With this constellation too, the latching body is advantageously formed by a stub-like projection which is arranged transversely to a pivoting plane of the grip pieces and is directed towards the path component. The latching receiver is then formed by a projection transversely to a pivoting plane but in the opposite direction, i.e. in the direction of the guide component. The latching body and the projection therefore each project transversely to pivoting planes of the grip pieces, but in the opposite direction.

A pivoting plane of the grip pieces is to be understood as a plane, in which the grip pieces lie on moving towards one another or on movement away from one another. Since the grip pieces are spatially extending components, a multitude of such imaged planes arise. Basically, it can herein also be the case of planes which are parallel thereto.

Concerning this constellation, with regard to which the latching body is arranged on the guide component and the latching receiver on the path component, it is particularly advantageous if the guide body is arranged at the end of the latching body and has a smaller cross section than the latching body. The latching body and guide body are then preferably formed by a stepped stub in an axially equal manner, wherein the stub section which is arranged on the guide component and is larger in cross section forms the latching body and the stub section which extends therefrom and is smaller in cross section forms the guide body.

It is particularly advantageous if, apart from the latching receiver, at least one guide surface is provided for the latching body, said guide surface guiding the latching body in a direction transverse to a pivoting plane of the grip pieces directly before and/or after reaching the latching position. In this manner, the guide body is decoupled from the guide path at the face side, so that this indeed yet merely needs to fulfil a purely path guidance function, whereas the at least one guide surface, apart from the latching receiver, assumes the control of the latching body in the direction of the stub axis—if this is designed as a stub.

For the functioning, it is basically of no significance as to whether the guide component or the path component is pivotably mounted on a grip piece. However, it is particularly advantageous to pivotably mount the guide component on the grip piece, since this is preferably provided as a narrow, flat component with the guide body close to the free end and is preferably designed in the manner of a leaf spring and is designed biased in the direction of the path component in the direction transverse to a pivoting plane of the grip pieces. The spring biasing ensures that the guide body always has contact with the base of the guide path and is thus controlled by the guide path in the direction transverse to the pivoting plane of the grip pieces. Concerning such an arrangement, it is particularly advantageous if the guide component is covered by a section of the handle or the grip piece in a direction transverse to a pivoting plane of the grip pieces and specifically in the direction opposite to the path component, thus at the side which is away from the path component. Such an arrangement ensures that the guide component is covered and therefore protected at least at one side, wherein this protection not only protects the component itself but also the operator from this component, and in particular prevents foreign bodies from penetrating into this region. To the other side, the guide component is at least partly covered and protected by the path component.

In order to ensure the targeted path control in only one direction also into the region, in which the guide body is no longer engaged with the base of the path guide, it is advantageous to arrange at least two or more guide surfaces next to the latching receiver such that a step is formed between them. This step which is then effective for the movement of the latching body prevents the latching body from moving in a path direction other than that which is envisaged, on its path for engagement with the latching receiver or out of this.

According to an advantageous further formation of the invention, the guide path is designed in a groove-like manner, thus typically lies in an extensive component such as a sheet metal for example, into which the guide path is milled or formed in another manner, wherein the groove base comprises oblique surfaces and steps which are provided for forming returns stops. The sides of this groove form the actual guide surfaces of the guide path. The groove base, on account of the steps, prevents the guide body which bears with is face side on the groove base and slides along there in the guide path from being moved backwards, thus opposite to the designated movement direction. Herein, oblique surfaces are provided and these bridge the ascent to a step. On running up such an oblique surface, the guide body is lifted until, after reaching the step, it is lowered again so that a return movement is prevented by the perpendicular edge of the step whose perpendicular surface lies parallel to the outer periphery of the guide stub if the guide body is designed as a stub.

According to the invention, the guide path advantageously comprises a peripheral path section, in which two equally directed deflecting regions are provided, in which a deflection of the path by more than 90 and less than 180 is effected, where an oppositely directed deflecting region is arranged lying therebetween.

A deflecting region in the context of the present invention is to be understood as a path section, in which a deflection, i.e. a direction change is effected. Given equally directed deflecting regions, the deflection is effected in the same direction, i.e. seen in the designated course of the path guidance either in the form of a deflection, thus curve to the right or in the form of a deflection thus a curve to the left. An oppositely directed deflection is to be understood in that this deflection, if the deflection arranged in front of this deflects to the right, this oppositely directed deflection now deflects to the left and vice versa.

According to a further development of the invention, the peripheral web section advantageously connects to a path section which forms a guide path on pivoting the grip pieces apart as well as on pivoting them together. Such a region lies outside the action latching mechanism and serves for guiding in both movement directions, thus in particular permits the grip pieces to also be able to be spread beyond the usual handing, but this being the case functionally independently of the latching mechanism, as can be necessary for example for connecting the shank and control rod with endoscopic instruments.

According to a further development of the invention, the return stops are arranged and aligned in the peripheral path section such that the guide path can only be traveled through in one direction, thus a defined movement sequence is effected.

According to an advantageous further development of the invention, concerning the medical instrument, the latching function can be disconnected, for example by way of the guide component being moved laterally, i.e. in a direction transverse to a pivoting plane of the grip pieces, by way of a lever which can be pivoted in or a displaceable body part, so that the guide body as well as the latching body disengage from the guide path or the latching receiver. Given a design of the guide component in the manner of a leaf spring, this can be effected in a simple manner by way of the guide component being set against its spring bias. For this, it is sufficient to attach a slider or lever on the inner side of the respective grip piece, said slider or lever distancing the guide component and path component from one another, for example by way of inserting a wedge.

The invention is hereinafter explained in more detail by way of embodiment examples which are represented in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a perspective plan view showing the path component of the instrument according to FIG. 1;

FIG. 4 is a perspective plan view showing the guide component of the instrument according to FIG. 1;

FIG. 5 is an enlarged perspective plan view showing the part of the path component of an alternative embodiment variant, said part forming the guide path;

FIG. 6 is a perspective plan view showing the guide component of this embodiment which can be brought into engagement with the path component according to FIG. 5;

FIG. 7 is an enlarged perspective plan view showing the part of the path component of a third embodiment; and FIG. 8 is a perspective plan view showing the associated guide component of the third embodiment.

DESCRIPTION OF THE PREFERRED EMBODIMENTS

Figure 1:
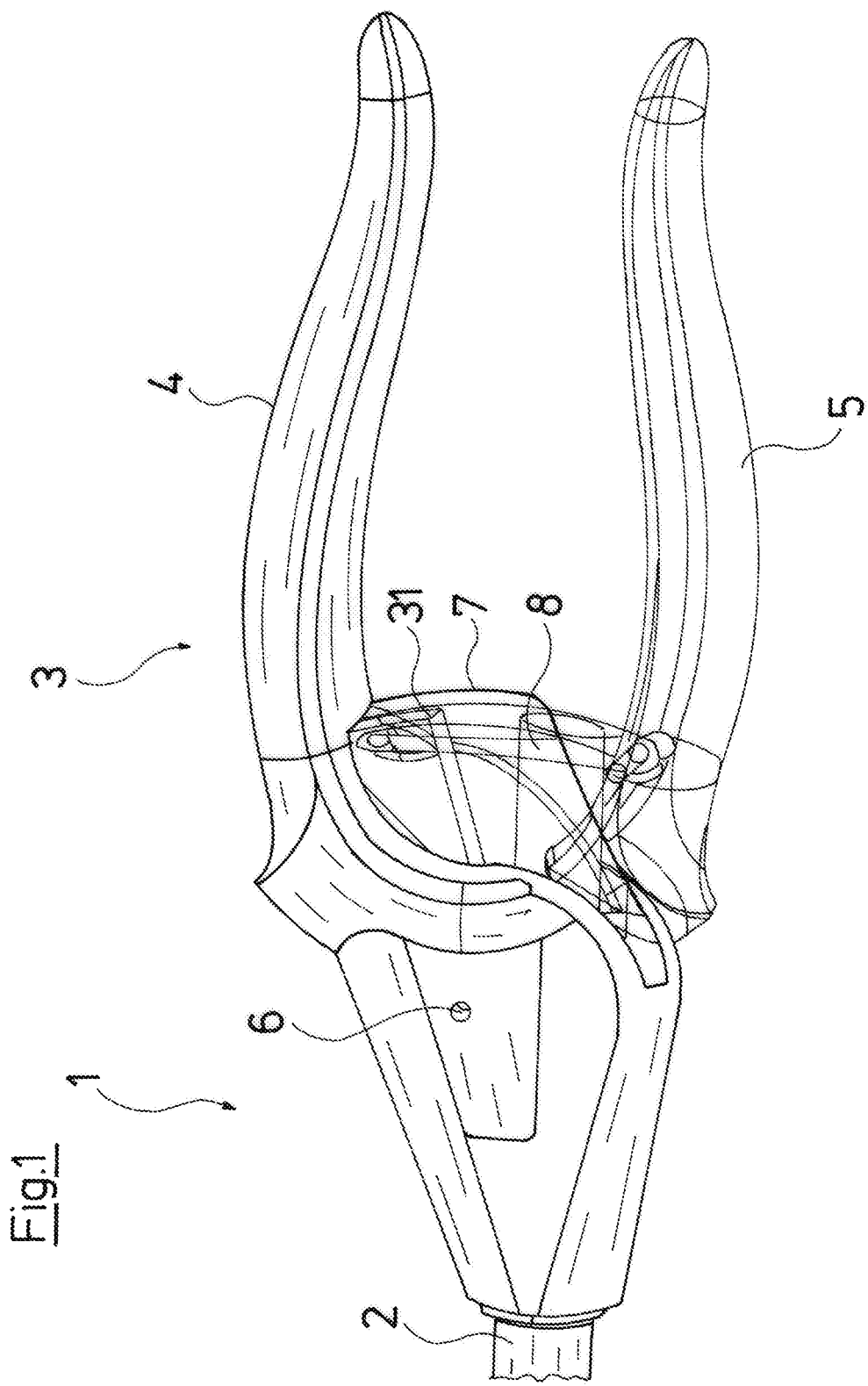
FIG. 1 is a greatly simplified transparent view showing the proximal part of an endoscopic needle holder.

Referring to the drawings, the instrument which is represented by way of the figures is an endoscopic needle holder 1, whose basic construction is counted as belonging to the state of the art. The actual tool, the needle holder is arranged at the distal end of a shaft 2 which is received in a proximal handle 3. The tool can be actuated via a control rod which is led in the shank 2, and the actuation is effected by way of the handle 3.

Concerning the represented embodiment, the handle 3 comprises a grip piece 4 which is rigidly connected to this handle 4, as well as a grip piece 5 which is mounted thereon in a pivotably movable manner and which is pivotable about a rotation axis 6. The grip piece 5 is loaded with spring force 5 in the opening direction with respect to the grip piece 4, and for this a helical torsion spring is incorporated within the handle 3 about the rotational axis 6, the ends of said spring at the one side being supported on the grip piece 4 and on the other side on the grip piece 5, so that the grip pieces are spring-biased counter to the closed position which is represented in FIG. 1. The tool is also closed in this closed position, i.e. a needle which is gripped by the needle holder is fixedly held.

The handle 3 latches in this closed position which is represented in FIG. 1, when the grip pieces 4 and 5 are pressed together as far as possible, typically by a hand gripping these, and then let go of. Only on renewed pressing together and subsequent letting go does the grip piece 5, due to the force of the biased spring, pivot with respect to the grip piece 4 about the rotation axis 6 until the distance of the proximal ends of the grip pieces 4 and 5 is at a maximum.

The latching mechanism is formed between the grip pieces 4 and 5 and comprises a path component 7 as well as a guide component 8 which is engaged with this. The path component 7 which is represented in detail in FIG. 3 is positively fixed on the grip piece 4, on the one hand by way of a bolt which forms the rotation axis 6 and which passes through a bore 9 and on the other hand by a positive-fit means which engages into an edge recess 10 and together with the fixation on the bore 9 ensures that the path component 7 is fixedly and rigidly connected to the grip piece 4. The path component 7 is plate-like and can be formed for example by way of a stainless steel sheet and comprises a guide path 11 which is yet described in detail further below, as well as a latching body in the form of a stub 12 which projects out with respect to the surface which is visible in FIG. 3 (out of the plane of the paper).

The path component 7 is actively connected to the guide component 8 which is represented in FIG. 4. In the installed position, the flat side of the guide component 8 which is visible in FIG. 4 faces the flat side of the path component 7 which is visible in FIG. 3. The guide component 8 is likewise designed as an extensive component, and specifically in the manner of a leaf spring. At its one end, it comprises a bore 13, with which it is pivotably fixed on the inner side of the grip piece 5, as is evident from FIG. 1. A guide body in the form of a guide stub 14 which rises perpendicularly from the extensive component 8 and has a cylindrical shape is arranged close to the free end of the guide component 8. This stub 14 extends perpendicularly to an imagined plane which is spanned on pivoting the grip piece 5 with respect to the grip piece 4 about the axis 6.

A recessed surface 15 which forms a guide surface and at the end is terminated by a latching receiver 16 which projects parallel to the stub 12 connects onto the stub 14 towards the free end of the guide component 8. This latching receiver 16 has the cross-sectional shape of a moon crescent whose outwardly directed arching (curvature) is formed by the rounded shape of the free end of the guide component 8 and whose retracted inner side lies opposite the stub 12. The shape of the guide component 8 is designed with an increasing material thickness but with a reducing width, from its grip-piece-side end close to the bore 13 up to the free end, in particular in the last third, so that the end at the grip-piece-side tends to assume a spring function, whereas the free end can be considered as being rigid.

Figure 2:
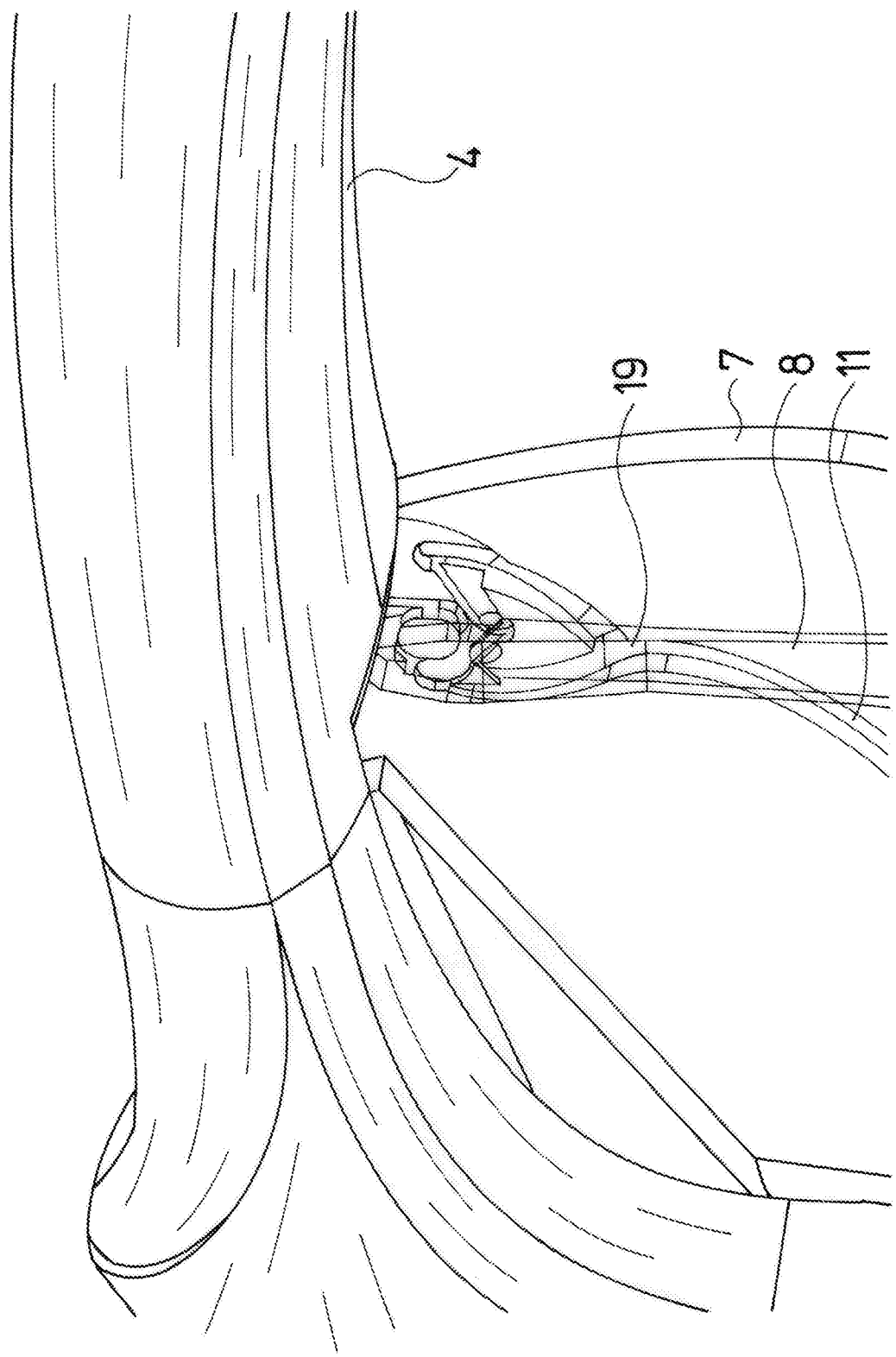
FIG. 2 is an enlarged representation showing the latching mechanism of the instrument according to FIG. 1.

The guide stub 14 projects significantly further than the projection which forms the latching receiver 16, so that in the installed position (see FIGS. 1 and 2), the stub 14 engages into the guide path 11 which laterally guides the stub 14. The guide stub 14 with its face side is pressed onto the base 17 of the guide path 11 by way of the spring force of the guide component 8 which is designed in the manner of a leaf spring. This base 17 runs in a plane manner and parallel to the component surface from a lateral inlet opening 8 up to the beginning 19 of a peripheral guide path section. This peripheral guide path section comprises two oblique surfaces 20, 21, specifically the oblique surface 20 which is at the right in FIG. 3 and which leads obliquely downwards from the beginning of the peripheral guide path section 19, i.e. into the plane of the paper of FIG. 3, to a lower level, and an oblique surface 21 which is at the left in FIG. 3 and which leads further upwards from a level 17 of the guide path 11.

On moving the grip pieces 4 and 5 apart, the guide stub 14 is moved along the guide path 11 to the beginning of the peripheral guide path section 19. A force which with respect to FIG. 3 acts to the left acts upon the stub 14 on account of its arrangement and this leads to the stub 14 getting into the branch of the peripheral guide section which is at the left in FIG. 3, on pressing the grip pieces 4 and 5 further together, in order there, firstly via the oblique surface 21, to be brought to a higher level. If the grip pieces 4 and 5 are maximally pressed together, then the guide stub 14 is located at the end of the part of the peripheral guide path section which is at the left in FIG. 3, said guide path section forming a deflecting region 22. Here, the guide path curves to the right in the designated run-through direction. If the grip pieces 4 and 5 are relieved of force on reaching this end position, then these are again moved a little bit apart due to spring force, wherein the guide stub 14 cannot run back into the region of the oblique surface 21 due to the overcome step 23, but runs through a short path region 24 until the stub 14 travels over a step 25, in which a latching position is formed, said latching position yet being described in detail further below. On pressing together the grip pieces 4 and 5 once again, the guide stub 14 runs through the second short path region 26 and finally gets via a step 27 into a deflecting region 28 which is separated from the short path region 26 by the step 27. If now the grip pieces 4 and 5 are again relieved of force, then the stub 14, since it is cannot get back into the short path region 26 on account of the step 27, travels over the oblique surface 20 again to the beginning 19 of the peripheral guide path section and from there onto the longitudinally extended part of the guide path 11. The guide stub 14 thus in the deflecting region 22 firstly curves to the right seen in the run-through direction, then goes through an oppositely directed deflecting region in the region of the step 25, thus does a left curve, in order to then run through a curve to the right in the deflecting region 28.

Concerning the described embodiment, the guide stub 14 which runs in the guide path 11 serves exclusively for the path guidance and not for the latching function. The latter is achieved by the latching body 12 in combination with the latching receiver 16, wherein it is of particular significance that the folding forces for the latching function are accommodated by these two components 12, 16 and not by the guide stub 14 and the guide path which, inasmuch as this is concerned, is load-free in the latching position. The latching stub 12 runs with little play outside the guide path 11 next to the guide stub 14 in a manner such that with the travel of the guide stub 14 through the peripheral guide section from the beginning 19 up to the deflecting region 22, the latching receiver 16 moves such that the latching stub 12 is arranged between the latching receiver 16 and the guide stub 14. If the guide stub 14 now travels along the short path region 24 up to the other side of the step 25, then the retracted inner side of the latching receiver 16 comes to bear on the latching stub 12. The guide stub 14 is relieved of force in this latching position. Herein, the recessed surface 15 which bears on the face side of the latching stub 12 also ensures a pressure relief of the guide stub 14 in the axial direction. Given a renewed pressing together of the grip pieces 4 and 5 and passing-through of the short path region 26, the latching receiver 16 is then moved over a step 29, onto which an oblique surface 30 connects, said oblique surface running out in the surface of the path component 7.

As can be derived from the schematic representations according to FIG. 1, the latching mechanism within the handle 3 is covered to one side by the smooth outer side of the path component 7 and to the other side by a protective covering 31, so that this region is practically not accessible from the outside, so that the latching function as well as the guide function lie completely protected in the region of the peripheral guide path.

Concerning the embodiment variant which is represented by way of FIGS. 5 and 6, a path component 7' and a guide component 8' are provided, said components differing from those which have been described above in that the step 29 and the oblique surface 30 of the path component 7 are absent in the path component 7', i.e. these regions can remain unmachined in the embodiment of the path component 7', but the step 25 is replaced by an oblique surface 34 within the guide path 11. In manner corresponding to this, the guide component 8' has no continuously recessed surface 15 but a surface 15', onto which a surface 32 at a higher level connects via a step 33. The surfaces 32 and 15' form guide surfaces and become effective as soon as these regions go over the face surface of the latching stub 12. Herein, the step 33 of the guide component 8' replaces the step 29 in the path component 7. This ensures that the latching stub 12 after overcoming the step 33 and amid the relief of the guide stub 14 gets into its defined position in the latching receiver 16 in a manner bearing on the recessed surface 15', from which position, on account of the step 33, it can only be moved in the direction of the guide stub 14 through the short path region 26 to the deflecting region 28. Herein, the oblique surface 34 ensures that the guide stub 14 is again led to a higher level, in order to then fall down the step 27 which blocks the rearward movement.

Embodiment variants of a path component 7" and of a guide component 8" are represented by way of FIGS. 7 and 8, wherein these embodiments differ from the embodiments described above in that the latching stub 12" as well as the guide stub 14" which connects at the face side onto the latching stub 12" in an axially equal manner is arranged on the guide component 8", whereas the latching receiver 16" is arranged on the path component 7". Concerning this embodiment variant, the guide function and latching function are likewise separated from one another. However, the guide stub 14" continues the latching stub 12" with a smaller cross section. Accordingly, guide surfaces 35, in which the face-side step of the latching stub 12" assumes the axial guidance are provided in the peripheral guide path section, and the stub 12" accommodates the forces in combination with the latching receiver 16", in the latching position While specific embodiments of the invention have been shown and described in detail to illustrate the application of the principles of the invention, it will be understood that the invention may be embodied otherwise without departing from such principles.

APPENDIX

List of Reference Numbers

1—endoscopic needle holder
2—shank
3—handle
4—rigid grip piece
5—movable grip piece
6—rotation axis/bolt
7, 7', 7"—path component
8, 8', 8"—guide component
9—bore
10—edge recess
11—guide path
12, 12"—latching body/latching stub
13—bore in the guide component
14—guide body/guide stub
15, 15'—recessed surface
16, 16'—latching receiver
17—base of the guide path
18—entry opening of the guide path
19—beginning of the peripheral guide section
20—right oblique surface
21—left oblique surface
22—left deflecting region
23—step
24—short path region
25—step
26—short path region
27—step
28—right deflecting region
29—step
30—oblique surface (guide surface)
31—protective covering
32—guide surface
33—step
34—oblique surface
35—guide surface

The invention claimed is:

1. A medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein the guide component is pivotably mounted on one of the two grip pieces; the guide component is configured as a leaf spring and is configured to be biased toward the path component, in a direction transverse to a pivoting plane of the two grip pieces.

2. The medical instrument according to claim 1, wherein the latching body is arranged on the guide component and the at least one latching receiver is arranged on the path component.

3. The medical instrument according to claim 2, wherein the latching body is formed by a stub projection transverse to a pivoting plane of the two grip pieces in a direction of the path component and the at least one latching receiver is formed by a projection transversely to a pivoting plane of the two grip pieces in a direction of the guide component.

4. The medical instrument according to claim 3, wherein the guide body is arranged at an end of the latching body and has a smaller cross section than the latching body.

5. The medical instrument according to claim 1, wherein, next to the at least one latching receiver, at least one guide surface is provided for the latching body, said at least one guide surface guiding the latching body in a direction transverse to the pivoting plane of the two grip pieces directly before and after reaching the at least one latching position.

6. The medical instrument according to claim 1, wherein at least two guide surfaces are arranged next to the at least one latching receiver, between which a step is formed.

7. The medical instrument according to claim 1, wherein the latching can be deactivated.

8. A medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein the latching body is arranged on the path component and the at least one latching receiver is arranged on the guide component; and the latching body is formed by a stub projection transverse to a pivoting plane of the two grip pieces in a direction of the guide component and the at least one latching receiver is formed by a projection transverse to the pivoting plane of the two grip pieces in a direction of the path component.

9. A medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein the guide component is pivotably mounted on one of the two grip pieces; the guide component is configured as a leaf spring and is configured so as to be biased towards the path component in a direction transverse to the pivoting plane of the two grip pieces; and the guide component is covered by a section of the proximal handle, in a direction transverse to a pivoting plane of the two grip pieces, opposite to the path component.

10. A medical instrument comprising: a proximal handle for controlling a distal tool, the handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein the guide path is configured as a groove, wherein a groove base of the groove comprises oblique surfaces which are stepped to one another for forming return stops; the guide path comprises a peripheral path section, in which two equally directed deflecting regions are provided, in which a deflection of the guide path of more than 90° and less than 180° is effected, and an oppositely directed deflecting region is arranged lying therebetween; the peripheral path section connects to a path section which forms the guide path on pivoting the two grip pieces apart as well as pivoting them together; and return stops are aligned and arranged in the peripheral path section such that the peripheral path section can only be traveled through in one direction.

11. A medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein the guide component is covered by a section of the proximal handle in a direction transverse to a pivoting plane of the two grip pieces, opposite to the path component.

12. The medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the two grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching same functionally independently of the guide body and guide path, wherein: the guide path is configured as a groove; a groove base of the groove comprises oblique surfaces which are stepped to one another for forming return stops; the guide path comprises a peripheral path section, in which two equally directed deflecting regions are provided, in which a deflection of the guide path of more than 90° and less than 180° is effected, and an oppositely directed deflecting region is arranged lying therebetween; and the peripheral path section connects to a path section which forms the guide path on pivoting the two grip pieces apart as well as pivoting them together.

13. A medical instrument comprising: a proximal handle for controlling a distal tool, the proximal handle comprising two grip pieces which are arranged pivotably movable relative to one another and subjected to a spring force; a path guide coupling movement of the two grip pieces, wherein the path guide comprises a path component which comprises a guide path; a guide component with a guide body on the guide component, said guide body engaging into the guide path, wherein the path component and the guide component are arranged on the two grip pieces and are subjected to the spring force relative to one another acting transversely to a pivoting plane of the grip pieces, one of the path component and the guide component is pivotably arranged on one of the two grip pieces and at least one latching position, in which a pivoting movement of the two grip pieces is blocked in one direction, is formed between the path component and the guide component; a latching body; and at least one latching receiver which receives the latching body in the at least one latching position, wherein the latching body and the at least one latching receiver are provided on the path component and the guide component for latching functionally independently of the guide body and guide path, wherein: the guide path is configured as a groove, wherein a groove base of the groove comprises oblique surfaces which are stepped to one another for forming return stops; the guide path comprises a peripheral path section, in which two equally directed deflecting regions are provided, in which a deflection of the guide path of more than 90° and less than 180° is effected, and an oppositely directed deflecting region is arranged lying therebetween; and return stops are aligned and arranged in the peripheral path section such that the peripheral path section can only be traveled through in one direction.

* * * * *